(12) United States Patent
Schertiger

(10) Patent No.: US 9,101,483 B2
(45) Date of Patent: Aug. 11, 2015

(54) OSTOMY BAG WITH INTERMEDIATE FILTER ELEMENT

(75) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 148 days.

(21) Appl. No.: 13/883,004

(22) PCT Filed: Nov. 7, 2011

(86) PCT No.: PCT/DK2011/050420
§ 371 (c)(1),
(2), (4) Date: May 2, 2013

(87) PCT Pub. No.: WO2012/062322
PCT Pub. Date: May 18, 2012

(65) Prior Publication Data
US 2013/0218111 A1 Aug. 22, 2013

(30) Foreign Application Priority Data

Nov. 8, 2010 (DK) .................................. 2010 70474

(51) Int. Cl.
*A61F 5/441* (2006.01)
*A61F 5/44* (2006.01)
(52) U.S. Cl.
CPC ....................................... *A61F 5/441* (2013.01)
(58) Field of Classification Search
CPC ........................................... A61F 5/44–5/4556
USPC .................................. 604/327, 328, 332–345
See application file for complete search history.

(56) References Cited

U.S. PATENT DOCUMENTS

| 4,579,658 | A | * | 4/1986 | Moller .......................... 210/483 |
| 4,875,899 | A | * | 10/1989 | Holtermann ................... 604/333 |
| 5,250,042 | A | * | 10/1993 | Torgalkar et al. ............. 604/333 |
| 5,306,264 | A | * | 4/1994 | Ferguson et al. ............. 604/333 |
| 5,348,546 | A | * | 9/1994 | Norton .......................... 604/333 |
| 5,370,638 | A | * | 12/1994 | Keyes ............................ 604/333 |
| 5,468,235 | A | * | 11/1995 | La Gro .......................... 604/333 |
| 5,667,502 | A | * | 9/1997 | Holtermann ................... 604/342 |
| 5,690,622 | A | * | 11/1997 | Smith et al. ................... 604/333 |
| 6,135,986 | A | * | 10/2000 | Leisner et al. ................ 604/322 |
| 6,506,184 | B1 | * | 1/2003 | Villefrance ................... 604/333 |
| 7,981,099 | B2 | * | 7/2011 | Butler ........................... 604/333 |
| 2007/0027434 | A1 | * | 2/2007 | Pedersen et al. ............. 604/333 |
| 2008/0306459 | A1 | * | 12/2008 | Albrectsen .................... 604/333 |
| 2010/0137821 | A1 | * | 6/2010 | Hansen et al. ................ 604/338 |
| 2010/0256581 | A1 | * | 10/2010 | Albrectsen .................... 604/333 |
| 2013/0072885 | A1 | * | 3/2013 | Luther et al. .................. 604/333 |
| 2013/0072886 | A1 | * | 3/2013 | Schertiger et al. ........... 604/333 |

FOREIGN PATENT DOCUMENTS

CN 101052363 10/2007
DE 3304312 6/1984
(Continued)

*Primary Examiner* — Susan Su
(74) *Attorney, Agent, or Firm* — Coloplast Corp, Coloplast A/S; Nick Baumann

(57) ABSTRACT

An ostomy bag (1) with a filter construction with an intermediate filter element (4) is provided. The intermediate filter element comprises a first wall (5) and a second wall (6) that, when the filter construction is positioned in the ostomy bag, is substantially parallel to the front and rear wall of the ostomy bag. The walls of the intermediate filter element include the gas-inlets for the filter construction. The intermediate filter element may be provided so that it constitutes an insert interposed between the rear wall and the front wall of the ostomy bag. The intermediate filter element may also be provided so that it constitutes a tube element.

6 Claims, 4 Drawing Sheets

(56) References Cited

FOREIGN PATENT DOCUMENTS

| | | |
|---|---|---|
| EP | 0235928 | 1/1987 |
| GB | 2031282 | 4/1980 |
| GB | 2124086 | 2/1984 |
| GB | 2371487 | 7/2002 |
| WO | 8806433 | 9/1988 |
| WO | 03071997 | 9/2003 |
| WO | 2007000167 | 1/2007 |

* cited by examiner

OSTOMY BAG WITH INTERMEDIATE FILTER ELEMENT

The invention relates to an ostomy bag having a filter construction with an intermediate filter element comprising a first wall and a second wall and where the inlets to the filter construction are positioned in the first and the second wall of the intermediate filter element.

BACKGROUND

In connection with surgery for a number of diseases in the gastro-intestinal tract, one of the consequences in many cases is that the patient is left with an abdominal stoma such as a colostomy or an ileostomy in the abdominal wall for the discharge of visceral contents. The discharge of visceral contents including intestinal gases cannot be regulated at will. For that purpose, the user will have to rely on an appliance to collect the material emerging from such opening in a bag, which is later emptied and/or discarded at a suitable time.

The discharge of flatus, measured in volume, may exceed the discharge of solid and liquid faecal matter by many hundreds of percent and therefore there is usually the need for the continuous or frequent venting of the intestine or the collecting bag. Normally the out-flowing flatus is deodorised with a suitable filter. Commonly, the active filter is powdered active carbon, which absorbs $H_2S$ being the principal component of the smell of flatus.

During use of a collecting bag, the output from a colostomy or an ileostomy may stick on the face of the filter facing inwards in the collecting bag. This will eventually lead to clogging of the filter, thereby reducing the flow through the filter. When the filter is completely blocked, it will stop functioning and the bag will fill with gases and expand, an effect also known as ballooning.

SUMMARY OF THE INVENTION

The invention relates to an ostomy bag with a filter construction with an intermediate filter element. The intermediate filter element comprises a first wall and a second wall that, when the filter construction is positioned in the ostomy bag, is substantially parallel to the front and rear wall of the ostomy bag. The walls of the intermediate filter element include the gas-inlets for the filter construction.

DETAILED DESCRIPTION OF THE INVENTION

In a first aspect, the invention relates to an ostomy bag with
a front wall
a rear wall with a waste inlet opening
an intermediate filter element having a first wall facing the rear wall of the ostomy bag and a second wall facing the front wall of the ostomy bag
at least one deodorising filter is positioned at the first wall or the second wall or in contact with both walls
where gas-inlets for the deodorising filter are provided in both the first wall and the second wall of the intermediate filter element.

By providing gas-inlets for the deodorising filter at both the first wall and the second wall, the risk of clogging both inlets at the same time is minimised. During use and when the user lies down, the output may flow up and cover the inlet on one side of the intermediate filter element. In that case the inlet on the other side (the other wall) of the intermediate filter element will still be open. Therefore, the deodorising filter will still work properly.

An ostomy bag is well-known in the art. It usually comprises a front wall and a rear wall of gas- and liquid impermeable foil-material (for example of polyethylene (PE), polyvinyl-chloride (PVC) or ethylene-vinyl-acetate (EVA)) that is welded around the edges or the rim so as to form a waste collection chamber. The bag may be welded only partly around the rim so that an opening for emptying the bag is provided at the lower end. In that case the bag may be provided with means for closing that opening. The bag includes a waste inlet opening, which at the outer side is provided either with mechanical or adhesive coupling means for coupling to a body side wafer or with a skin-friendly adhesive adapted for direct adhering to the abdomen of the user.

The ostomy bag may be either welded around the entire rim or it may have an emptying device at the bottom of the bag, for example in the form of a closable outlet, which is well-known in the art.

Usually, the waste inlet opening is placed in the upper part of the ostomy bag so that when a user stands up, the waste inlet opening will be above the midline of the ostomy bag. This leaves a larger collecting volume below the waste inlet opening. The longitudinal direction of the bag is defined as the direction from the upper part of the bag towards the lower collecting volume. The transverse direction is defined as transversely thereto.

Thus, in an embodiment the ostomy bag may have
a top portion defined as the portion generally above the waste inlet opening, when the bag is worn on the skin of the user
a bottom portion defined as the portion generally below the waste inlet opening, when the bag is worn on the skin of the user In this embodiment, the intermediate filter element may be placed in a position at the waste inlet opening or generally above the waste inlet opening of the bag, Due to gravity the output will have a tendency to fall towards the bottom portion during use—that is be stored or kept below the waste inlet opening. Thus, providing the intermediate filter element generally at or above the waste inlet opening of the bag ensures that most of the output will be kept out of contact with the intermediate filter element.

The deodorising filter, or filter or deodorising element, may be provided as filter packages typically used for ostomy bags. The filter construction may include more than one deodorising filter, such as two, three or more. As an example, a filter package like Filtrodor® from Coloplast A/S may be used. This filter package comprises a disc-shaped foam element where the foam is impregnated in carbon. The foam element is covered with a gas-impermeable foil on both sides of the disc, except for a hole punched centrally in one of the foils. This hole functions as a gas-outlet to the deodorising filter and the periphery of the element functions as a gas-inlet. The gas-flow direction through the deodorising filter may also be opposite, so that gas enters the deodorising filter centrally and exits at the periphery. When the gas has travelled the distance from the periphery of the disc to the centre (or vice-versa), it is adequately deodorised. The diameter of such an element is at least 25 mm but may be larger if needed.

The deodorising filter may also be of elongated shape with an inlet in one end and an outlet in the other. Such a deodorising filter may be of the type described in European Patent no. 0235928B1.

In an embodiment, the first wall of the intermediate filter element is welded to the rear wall of the ostomy bag and the second wall is welded to the front wall of the ostomy bag.

In a further embodiment, the intermediate filter element constitutes an insert interposed between the rear wall and the front wall of the ostomy bag so that the top portion of the bag comprises four layers of foil constitutina a concertina structure the first and second wall are welded together at a connection zone the first and second wall have a rounded top portion generally corresponding to the top portion of the ostomy bag, the first wall being welded to the rear wall along the rounded top portion the second wall being welded to the front wall along the rounded top portion.

In this embodiment, the intermediate filter element and the front and rear wall together constitute an ostomy bag with an expandable top portion, thus also allowing for expansion of the top of the bag in situations with excess gas building up inside the bag. In cross-section, the expandable top portion would look like a V-shape with the ends of the leg attached to the front wall and rear wall respectively and the connection point lying in between the front wall and rear wall. The ostomy bag may include at least two deodorising filters with separate inlets, one in each first or second wall.

By rounded top is meant that the first and second walls generally have the same shape as the top portion of the ostomy bag.

In an embodiment, the intermediate filter element is welded around a piece of foam so that in use the foam prevents the rear and front walls of the bag from collapsing or pancaking and thereby providing a free gas passage. Furthermore, the foam element acts as a stopper towards any output from reaching the deodorising filter(s) when the user is lying down. This is because the output has to climb over the obstacle provided by the foil encapsulated foam piece.

In another embodiment, the intermediate filter element constitutes a tube element.

In this embodiment, the first and second wall are initially welded or glued to each other so as to form a tube, then holes and filters are provided on the tube and then the tube element is placed between the front wall and the rear wall of the ostomy bag. The tube is subsequently welded or glued to the ostomy bag so that the ends of the tube are attached via the welding in the contour welding of the ostomy bag. A tube element passing transversely through the bag from one side to the other is thus formed. When the contour of the ostomy bag is welded across the tube-ends, the tube-ends are preferably prevented from welding to each other. This may for example be done by inserting an element in the tube. Thereby, the tube element provides gas-outlets or vents where the tube ends are attached to the bag.

This tube element may be placed directly across from the waste inlet opening. In this situation, the tubular element may protect the stoma from impacts at the front of the bag. Furthermore, if the sides of the tube element were positioned so they could get in contact with stoma (through the ostomy bag), this might lead to irritation of the stoma.

BRIEF DESCRIPTION OF THE DRAWING

FIG. 1 illustrates an ostomy bag according to the invention, in which the intermediate filter element constitutes an insert.

FIG. 3 illustrates an ostomy bag according to the invention, in which the intermediate filter element constitutes a tube element.

DETAILED DESCRIPTION OF THE DRAWING

Figures 1A, 1B:
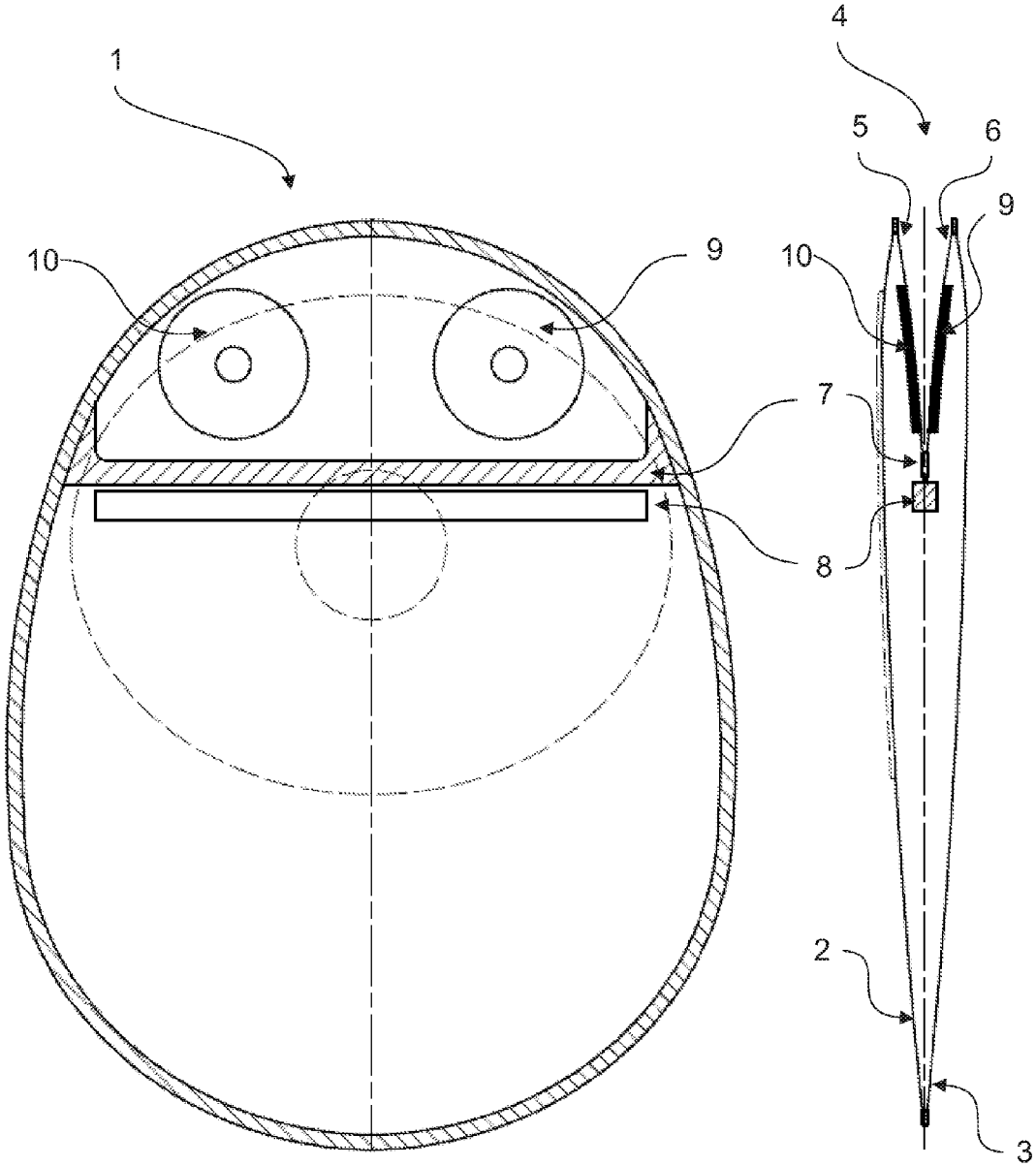
FIG. 1A illustrates the ostomy bag seen from the rear side of the ostomy bag and FIG. 1B illustrates the ostomy bag seen from the side.

FIGS. 1A and 1B illustrate an ostomy bag 1 according to an embodiment of the invention. The ostomy bag 1 comprises a front wall 2 and a rear wall 3. In the embodiment in FIG. 1, the ostomy bag is shown as a closed bag—however, the bag may be provided with a drainage opening at the bottom of the bag. An intermediate filter element 4 is provided at the top if the bag with a first wall 5 facing the rear wall 3 of the bag (that is, the first wall 5 faces in the direction of, or toward, the rear wall 3 of the bag) and a second wall 6 facing the front wall 2 (i.e., the first wall 5 in closer to the front wall 2 of the ostomy bag 1 than the second wall 6 if to the front wall 2 of the ostomy bag). The first wall 5 and the second wall 6 are welded together along a connection zone 7. In the embodiment shown in this figure, the connection zone 7 includes a foam element 8 functioning as an extra security preventing output from reaching the intermediate filter element 4.

Deodorising filter elements 9, 10, are positioned at the intermediate filter element 4. In this embodiment, two deodorising filters 9, 10 are used, one positioned at the first wall 5 and the other positioned at the second wall 6. In the embodiment shown, the deodorising filters 9, 10 are positioned on the inside of the walls 5, 6, however, they may also be positioned on the outside of the walls 5, 6.

The deodorising filter elements 9, 10 may include a microporous membrane (not shown) on the side facing inwards in the bag. This membrane will help protect the deodorising filter from getting into contact with the liquid elements of the output.

Figure 2:
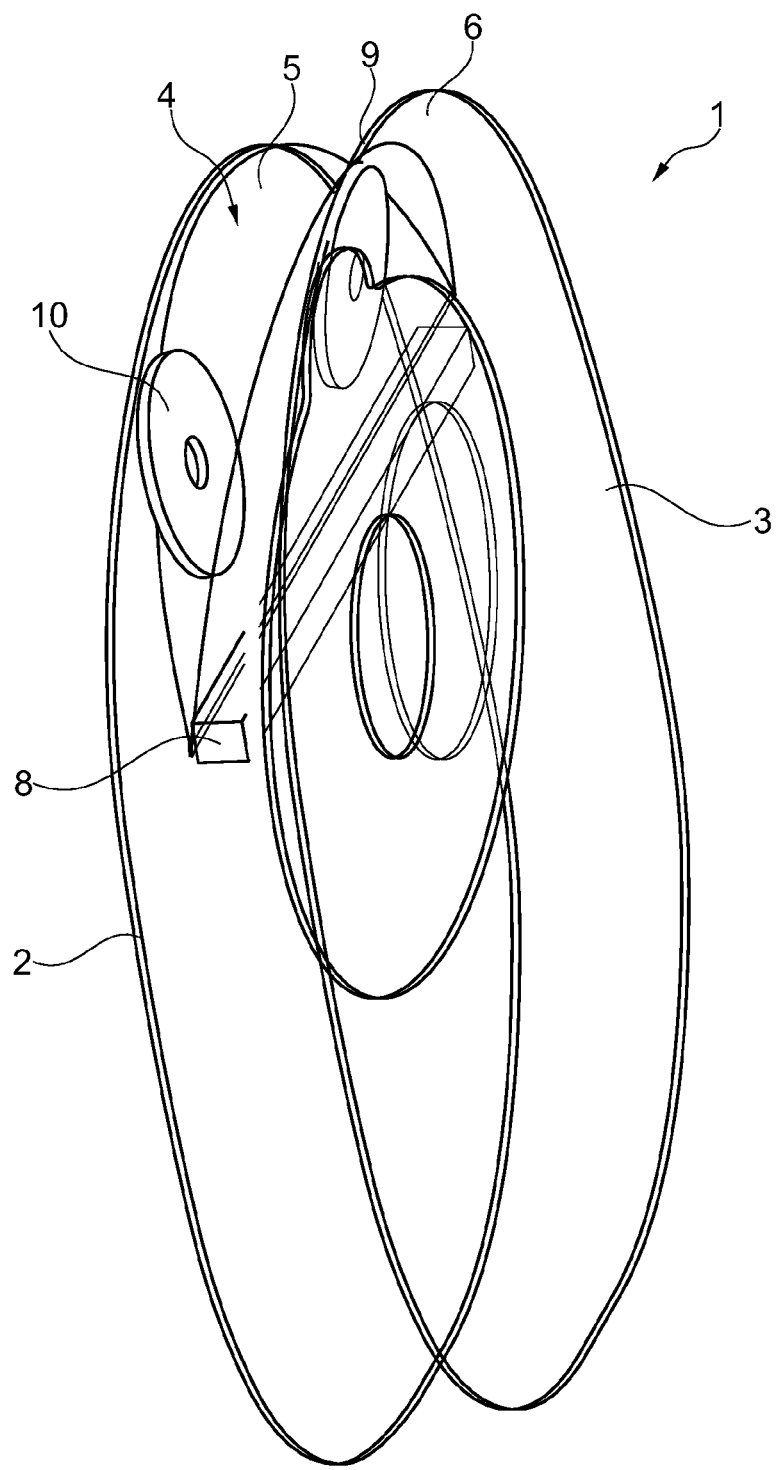
FIG. 2 illustrates an ostomy bag corresponding to FIG. 1 seen in perspective.

FIG. 2 illustrates the same ostomy bag as in FIG. 1. In FIG. 2, the bag 1 is shown in perspective, so it is easier to see the positioning of the foam element 8 and the deodorising filters 9, 10. However, in FIG. 2 the front wall and rear wall of the ostomy bag are shown prior to welding them along their contour. Thus, the ostomy bag is not shown in a state where it is ready to be used.

Figures 3A, 3B:
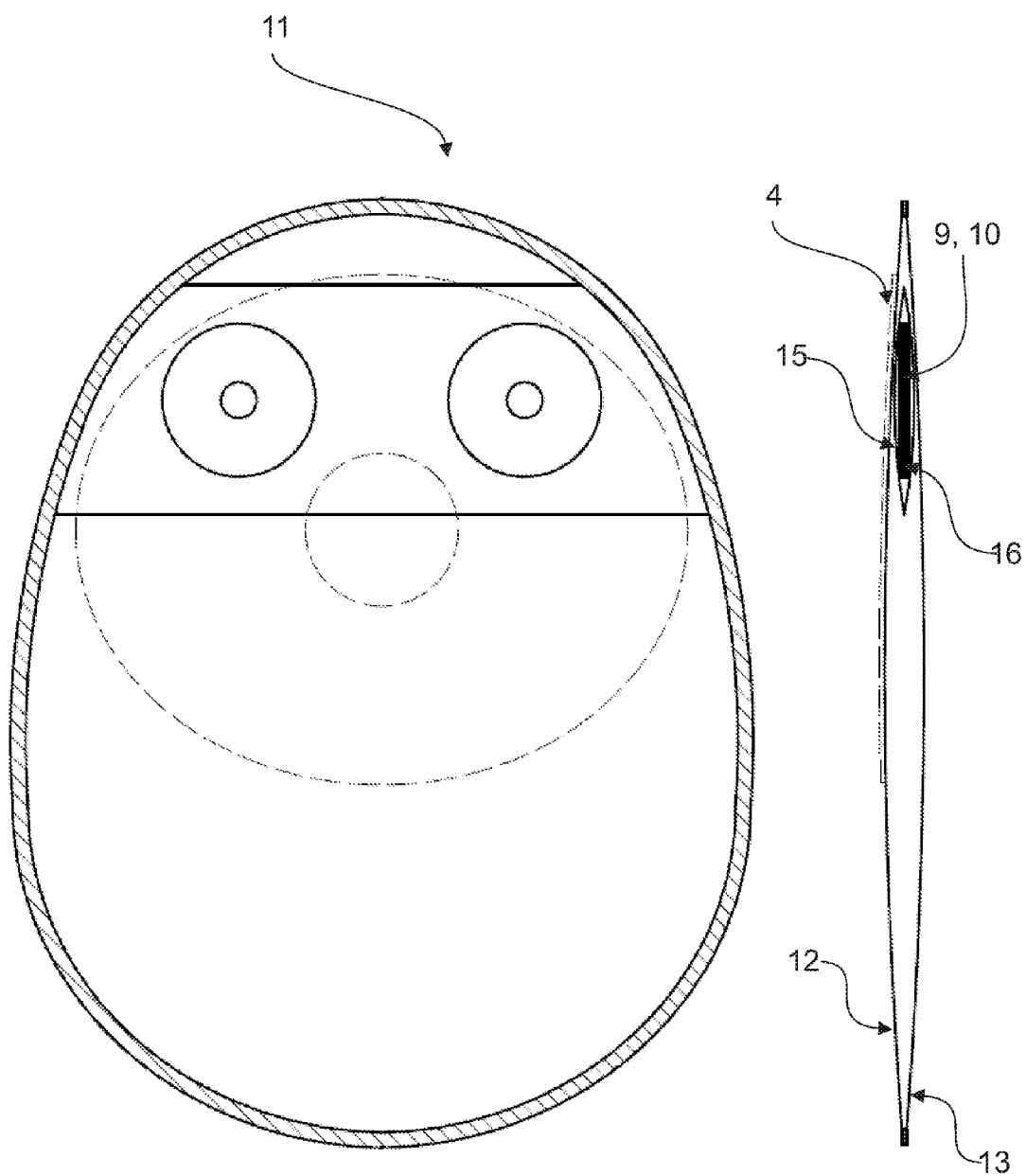
FIG. 3A illustrates the ostomy bag seen from the rear side of the ostomy bag and FIG. 3B illustrates the ostomy bag seen from the side.

FIGS. 3A and 3B illustrate another embodiment of an ostomy bag 11 according to the invention. This ostomy bag 11 also comprises a front wall 13 and a rear wall 12. The intermediate filter 14 is, in this embodiment, made as a tube element comprising a first wall rear-wall facing part 15 and a second front-wall facing part 16. The first wall 15 and the second wall 16 are welded together at the top and bottom to form the tube element. Two deodorising filters 9, 10 are positioned inside the tube element that is on the outside of the first wall 15 and second wall 16, respectively. The inside of the first wall 15 and the second wall 16 is defined as the side facing into the bag. The tube element may extend from one side of the bag to the other. In this embodiment, the gas vents may be provided where the tube element is attached to the sides of the bag, for example by not welding the tube foils (the first and second wall) together at the side of the bag.

Figure 4:
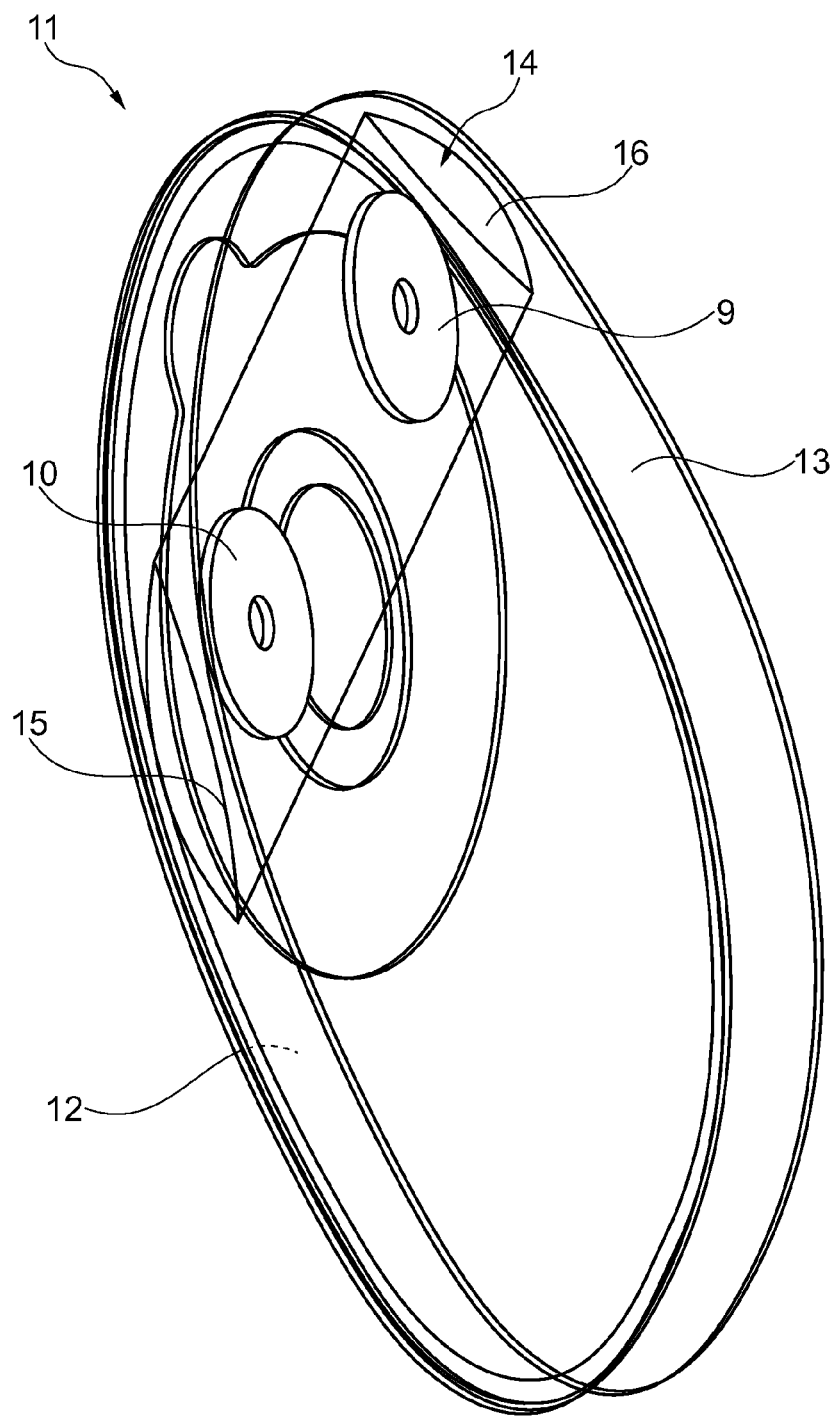
FIG. 4 illustrates an ostomy bag corresponding to FIG. 3 seen in perspective.

FIG. 4 illustrates the same ostomy bag as seen in FIGS. 3A and 3B seen in perspective. Like with FIG. 2, the front wall and rear wall of the ostomy bag are shown prior to welding them along their contour. Thus, the ostomy bag is not shown in a state where it is ready to be used.

The invention claimed is:

1. An ostomy bag with
   a front wall,
   a rear wall with a waste inlet opening,
   an intermediate filter element having a first wall and a second wall, with the first wall closer to the front wall of the ostomy bag than the second wall is to the front wall of the ostomy bag, and
   at least one deodorising filter is positioned at the first wall or the second wall of the intermediate filter element or in contact with both the first wall and the second wall of the intermediate filter element;
   wherein gas-inlets for the deodorising filter are provided in both the first wall and the second wall of the intermediate filter element;
   wherein the first wall of the intermediate filter element is connected to the rear wall of the ostomy bag by a connection zone of the intermediate filter element and the second wall of the intermediate filter element is connected to the front wall of the ostomy bag by the connection zone of the intermediate filter element; and
   wherein the intermediate filter element is an insert interposed between the rear wall and the front wall of the ostomy bag so that
   a top portion of the ostomy bag has four layers of foil formed as a concertina structure,
   the first wall and the second wall of the intermediate filter element are welded together at the connection zone;
   wherein the first wall and the second wall of the intermediate filter element have a rounded top portion generally corresponding to the top portion of the ostomy bag, with the first wall of the intermediate filter element connected to the rear wall by the rounded top portion and the second wall of the intermediate filter element connected to the front wall by the rounded top portion.

2. An ostomy bag according to claim 1, wherein the top portion of the ostomy bag is located above the waste inlet opening and
   a bottom portion of the ostomy bag is located below the waste inlet opening; when the bag is worn on the skin of the user;
      wherein the intermediate filter element is placed in a position at or above the waste inlet opening of the bag.

3. An ostomy bag according to claim 1, wherein the connecting zone of the intermediate filter element is welded around a piece of foam.

4. An ostomy bag according to claim 1, wherein the intermediate filter element constitutes a tube element.

5. An ostomy bag according to claim 4, wherein tube ends of the tube element are attached via a welding in a contour welding of the ostomy bag so that the tube element passes through the bag.

6. An ostomy bag according to claim 5, wherein the tube element provides vents where the tube ends are attached to the bag.

* * * * *